United States Patent
Kimura

(10) Patent No.: US 9,909,096 B2
(45) Date of Patent: Mar. 6, 2018

(54) DETECTOR INCLUDING TOUCHSCREEN SENSOR TO DETECT SIGNALS FROM CELLS IN A CULUTURE VESSEL. CULTURE VESSEL INCLUDING A TOUCHSCREEN SENSOR,AND CELL DETECTING METHOD

(71) Applicant: OLYMPUS CORPORATION, Shibuya-ku, Tokyo (JP)

(72) Inventor: Hiroyuki Kimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/644,055

(22) Filed: Mar. 10, 2015

(65) Prior Publication Data

US 2015/0259640 A1 Sep. 17, 2015

(30) Foreign Application Priority Data

Mar. 12, 2014 (JP) .................................. 2014-048734

(51) Int. Cl.
| | |
|---|---|
| *C12M 1/34* | (2006.01) |
| *C12M 3/00* | (2006.01) |
| *C12Q 1/02* | (2006.01) |
| *C12M 1/36* | (2006.01) |

(52) U.S. Cl.
CPC ............ *C12M 41/36* (2013.01); *C12M 23/44* (2013.01); *C12M 41/12* (2013.01); *C12M 41/46* (2013.01); *C12M 41/48* (2013.01); *C12Q 1/02* (2013.01)

(58) Field of Classification Search
None
See application file for complete search history.

(56) References Cited

U.S. PATENT DOCUMENTS

| | | |
|---|---|---|
| 2005/0051723 A1 | 3/2005 | Neagle et al. |
| 2005/0153425 A1 | 7/2005 | Xu et al. |
| 2007/0172939 A1 | 7/2007 | Xu et al. |
| 2012/0142031 A1 | 6/2012 | Xu et al. |
| 2012/0214225 A1 | 8/2012 | Oura et al. |
| 2013/0017567 A1 | 1/2013 | Lu et al. |

FOREIGN PATENT DOCUMENTS

| | | |
|---|---|---|
| EP | 2489435 A2 | 8/2012 |
| JP | 2012080869 A | 4/2012 |
| WO | 2005009126 A1 | 2/2005 |
| WO | 2005047482 A2 | 5/2005 |

OTHER PUBLICATIONS

"Cell and tissue culture," Sarstedt Product Guide.*
Extended European Search Report dated Jul. 29, 2015, issued in counterpart European Application No. 15158399.4.

* cited by examiner

*Primary Examiner* — David W Berke-Schlessel
(74) *Attorney, Agent, or Firm* — Holtz, Holtz & Volek PC

(57) ABSTRACT

In order to determine the culturing state of cells in a culture vessel in a simple manner at an appropriate timing without removing the culture vessel from the culturing apparatus, a cell culturing apparatus includes a culturing chamber that accommodates a culture vessel, which can accommodate cells in the interior thereof, and that maintains a predetermined temperature and humidity; a touchscreen sensor that is disposed inside the culturing chamber on a mounting surface, on which the culture vessel is placed, and that is brought into tight contact with an external surface of a bottom of the culture vessel; and an output portion that exports an output from the touchscreen sensor to the exterior of the culturing chamber.

23 Claims, 4 Drawing Sheets

DETECTOR INCLUDING TOUCHSCREEN SENSOR TO DETECT SIGNALS FROM CELLS IN A CULUTURE VESSEL. CULTURE VESSEL INCLUDING A TOUCHSCREEN SENSOR, AND CELL DETECTING METHOD

CROSS-REFERENCE TO RELATED APPLICATIONS

This application is based on Japanese Patent Application No. 2014-048734, the contents of which are incorporated herein by reference.

TECHNICAL FIELD

The present invention relates to a cell culture vessel, a cell culturing apparatus, and a cell culturing method.

BACKGROUND ART

In order to determine the timing for transferring cells or ending culturing of cells, the culturing state and proliferation state of cells are checked. To check the culturing state and the proliferation state of cells that are adhered to the bottom of a culture vessel, an adhesion area is measured by means of observation from outside a transparent culture vessel by using a microscope or the like (for example, see Patent Literature 1). To measure an adhesion area, an observer makes a count while visually observing an image of the cells acquired via an ocular lens of the microscope, or numerical data are acquired by using a determining program to analyze an image of the cells acquired by using the microscope.

To check the culturing state and the proliferation state of the cells, the cells that are being cultured in a culturing apparatus must be removed from the culturing apparatus together with the entire culture vessel, which is then placed in the microscope. In other words, when, as a result of microscope observation, the culturing state and the proliferation state are not satisfactory, it is necessary to return the culture vessel into the culturing apparatus again and to continue the culturing, and thus, the work performed is wasted and the risk of contamination by other cells such as bacteria or the like and other contaminants such as viruses or the like is increased. On the other hand, if the culturing state and the proliferation state are not checked at an appropriate timing, there is a risk of missing the appropriate timing for transferring the cells.

CITATION LIST

Patent Literature

{PTL 1} Japanese Unexamined Patent Application, Publication No. 2012-80869

SUMMARY OF INVENTION

An aspect of the present invention is a cell culturing apparatus including a culturing chamber that accommodates a culture vessel; a touchscreen sensor that is disposed inside the culturing chamber on a mounting surface, on which the culture vessel is placed, and that is brought into tight contact with an external surface of a bottom of the culture vessel; and an output portion that exports an output from the touchscreen sensor to an exterior of the culturing chamber.

DESCRIPTION OF EMBODIMENT

A cell culturing apparatus 1 and a cell culturing method according to an embodiment of the present invention will be described below with reference to the drawings.

Figure 1:
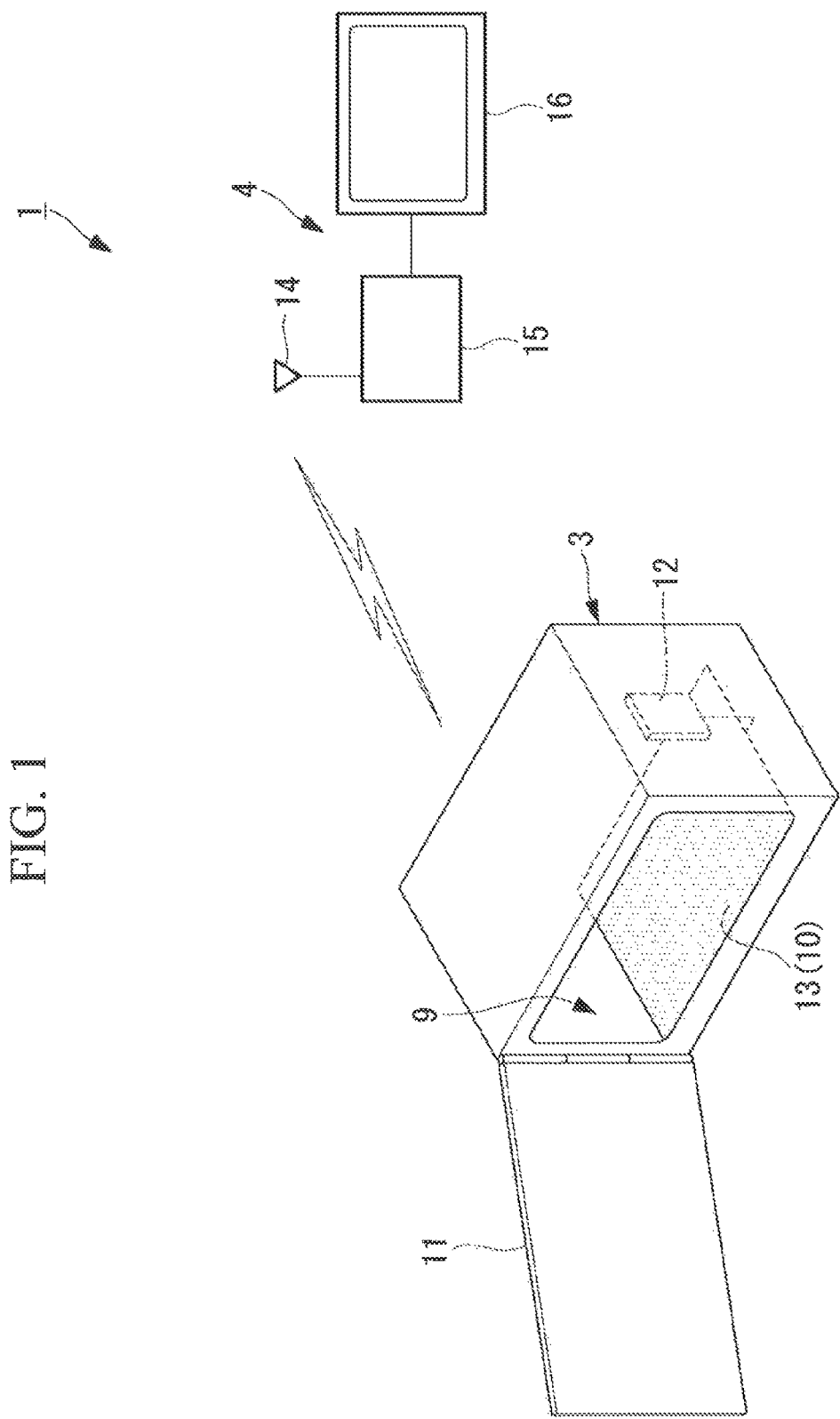
FIG. 1 is an overall configuration diagram of a cell culturing apparatus according to an embodiment of the present invention.
Figure 2:
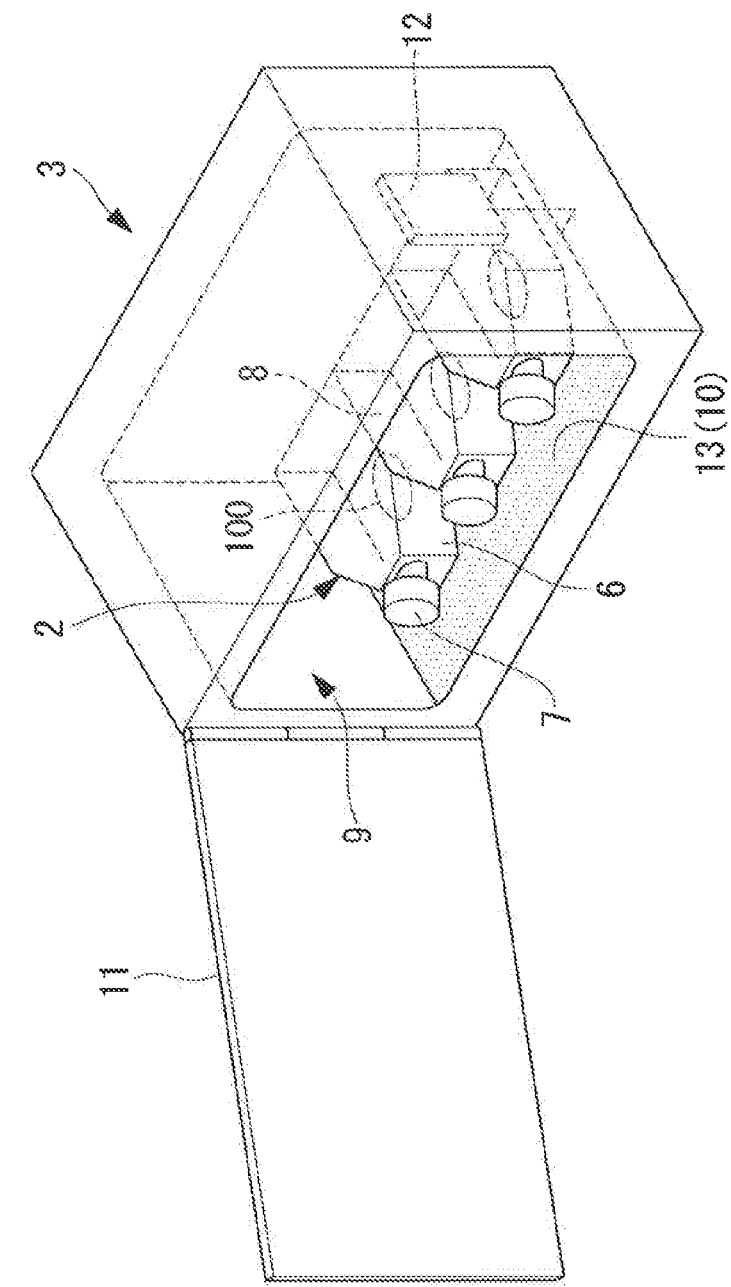
FIG. 2 is a diagram showing a state in which a culture vessel is accommodated in an apparatus main unit of the cell culturing apparatus in FIG. 1.

As shown in FIGS. 1 and 2, the cell culturing apparatus 1 according to this embodiment is provided with an apparatus main unit 3 that accommodates culture vessels (cell culture vessels) 2 that accommodate cells 100 in the interior thereof and that maintain the conditions thereof at predetermined temperature and humidity, thereby culturing the cells 100, and an analyzing portion 4 that is disposed remote from the apparatus main unit 3 and that analyzes the states of the cells 100 being cultured in the apparatus main unit 3.

As shown in FIG. 2, each culture vessel 2 has an opening 5 at one end thereof and is provided with a vessel main unit 6 that can accommodate the cells 100 in the interior thereof and a lid 7 that is attached to the opening 5 to seal the vessel main unit 6.

The vessel main unit 6 is formed of an optically transparent member (for example, a resin such as polystyrene or the like or PDMS (poly dimethylsiloxane) or the like or other material such as glass or the like), and a bottom 8 of the vessel main unit 6 on which the cells 100 are placed is constituted of a thin membrane-like film. With this thin membrane-like film, it suffices that the thickness thereof be such that an adhesion position and an adhesion area of the cells 100 adhered to the opposite surface of the film can be detected through the film by using a touchscreen sensor 13. It is preferable that the thickness of the film constituting the bottom 8 be 150 μm±50 μm. In addition, with regard to the material for the film also, it suffices that the material be such that the adhesion position and the adhesion area of the cells 100 can be detected through the film by using the touchscreen sensor 13. The material for the film is, for example, PET (polyethylene terephthalate), silicone, or the like.

As shown in FIGS. 1 and 2, the apparatus main unit 3 is provided with a culturing chamber 9 that has, as a bottom thereof, a mounting surface 10 on which a plurality of culture vessels 2 can be mounted and a door 11 that opens and closes the culturing chamber 9. The touchscreen sensor 13 is disposed at the mounting surface 10.

As shown in FIGS. 1 and 2, the touchscreen sensor 13 is a single flat sensor based on a resistive membrane system that is large enough that the plurality of culture vessels 2 can be placed next to each other and to which the bottoms 8 of all culture vessels 2 can be brought into tight contact over the entire area thereof. The touchscreen sensor 13 has a sensitivity that allows detection, through the bottoms 8, of the adhesion positions of the cells 100 that adhere to and grow on the bottoms 8 of the culture vessels 2. In addition, it is preferable that the resolution of the touchscreen sensor 13 be about 10 nm.

Specifically, the touchscreen sensor 13 is configured to detect the positions of the cells 100 based on pressure exerted thereon from the cells 100 that are adhered to the top surfaces (internal surfaces) of the bottoms 8 of the culture vessels 2.

In this embodiment, because the plurality of culture vessels 2 are mounted on the single touchscreen sensor 13, a detection region of the touchscreen sensor 13 is divided so as to correspond to the culture vessels 2, and the positions of the cells 100 are detected for the respective divided detection regions.

In addition, the cell culturing apparatus 1 according to this embodiment is provided with a transmitting portion (output portion) 12 that wirelessly transmits the positional information of the cells 100 detected by the touchscreen sensor 13 to the exterior.

As shown in FIG. 1, the analyzing portion 4 is provided with a receiving portion (input portion) 14 that receives the positional information of the cells 100 transmitted thereto from the transmitting portion 12, a determining portion 15 that determines the culturing states of the cells 100 in the individual culture vessels 2 based on the information signals from the touchscreen sensor 13 received by the receiving portion 14, and a monitor 16 that displays the culturing states determined by the determining portion 15.

The receiving portion 14 receives the positional information of the cells 100 wirelessly transmitted thereto from the transmitting portion 12 and inputs this information to the determining portion 15.

The determining portion 15 calculates the adhesion areas of the cells 100 adhered to the bottoms 8 based on the positional information of the cells 100 detected by the touchscreen sensor 13. The determining portion 15 determines whether or not the calculated adhesion areas of the cells 100 have reached a predetermined set area, and outputs the determination result on the monitor 16 as the culturing states of the cells 100.

The operation of the thus-configured cell culturing apparatus 1 and the cell culturing method of this embodiment will be described below.

To culture cells by using the cell culturing apparatus 1 according to this embodiment, first, the lid 7 is removed from the opening 5 of the culture vessel 2, whose interior is kept sterile, the cells 100 are introduced into the vessel main unit 6 from the opening 5 together with culture liquid (not shown), and the lid 7 is attached to the opening 5, thus sealing the culture vessel 2 (step of accommodating the cells 100 in the culture vessel 2).

As shown in FIG. 2, a plurality of culture vessels 2 in which the cells 100 are accommodated in this way are placed next to each other on the mounting surface 10 of the culturing chamber 9 so that the bottoms 8 thereof face downward. By doing so, the bottoms 8 of all culture vessels 2 are brought into tight contact with the touchscreen sensor 13 provided at the mounting surface 10.

At this time, because the touchscreen sensor 13 is divided in the plurality of regions and detection is performed for the respective regions, the individual culture vessels 2 are arranged so as to be positioned in different regions. Then, the door 11 of the culturing apparatus is closed and the culturing chamber 9 is sealed (step of accommodating the culture vessels 2 in the culturing chamber 9).

In this state, the cells 100 are cultured by maintaining the interior of the culturing chamber 9 at the predetermined temperature and humidity. Even if the cells 100 in the culture vessels 2 are initially floating in the culture liquid, as culturing advances, the cells 100 adhere to the bottoms 8 of the culture vessels 2, which facilitates the growth thereof, thus proliferating along the bottoms 8 of the culture vessels 2.

Once the cells 100 adhere to the bottoms 8 of the culture vessels 2, the adhesion positions of the cells 100 are detected by the touchscreen sensor 13 through the bottoms 8 of the culture vessels 2. The detected information about the adhesion positions of the cells 100 is separately output to the transmitting portion 12 for the respective regions of the touchscreen sensor 13 and is wirelessly transmitted by the transmitting portion 12 to the exterior of the culturing apparatus 1.

The transmitted information about the adhesion positions of the cells 100 is received by the receiving portion 14 and is input to the determining portion 15. Then, the determining portion 15 calculates the adhesion areas of the cells 100 for the respective culture vessels 2 based on the input information about the adhesion positions, and determines whether or not the calculated adhesion areas of the cells 100 have reached the predetermined area. Then, the determination result from the determining portion 15 is displayed on the monitor 16 as the culturing states of the cells 100 (step of observing).

Specifically, with the cell culturing apparatus 1 and the cell culturing method according to this embodiment, there is an advantage in that it is possible to check the culturing states of the cells 100 in the culturing vessels 2 in a simple manner at an appropriate timing without removing the culture vessels 2 from the culturing chamber 9.

In this case, there is an advantage in that, when the adhesion areas of the cells 100 reach the predetermined area, an observer can accurately ascertain in which culture vessels 2 the culturing of the cells 100 has finished based on the respective positional information of the cells 100 for the individual detection regions that are divided so as to correspond to the culture vessels 2.

Note that, in this embodiment, examples of the cells 100 to be cultured in the culture vessels 2 include embryonic stem cells, induced pluripotent stem cells, stem cells (derived from bone marrow, fat, muscle, nerve, liver, placenta, umbilical cord blood, or peripheral blood), chondrocytes, hepatocytes, osteocytes, skin cells, myocardial cells, skeletal muscle cells, vascular endothelial cells, nerve cells, and so forth.

In addition, in this embodiment, although a sensor based on the resistive membrane system has been described as an example of the touchscreen sensor 13, it is not limited thereto, so long as the culturing states of the cells 100 can be detected. For example, a sensor based on an ultrasonic surface acoustic wave system may be employed as the touchscreen sensor 13. In addition, the bottoms 8 of the culture vessels 2 may be constituted of a thin membrane-like film having transparent conductivity, and a sensor based on a capacitive sensing system, an electromagnetic induction system, or an infrared optical imaging system may be employed. In other words, it suffices that the touchscreen sensor 13 be a sensor that can detect the adhesion positions of the cells 100 by detecting, through the thin membrane-like film, pressure signals, electrical signals, electromagnetic wave signals, or the like from the cells 100 that are adhered to the opposite surface of the film.

In addition, in this embodiment, although a case in which the determining portion 15 that determines the culturing states of the cells 100 based on the calculated adhesion areas of the cells 100 serves as the analyzing portion 4 has been described as an example, it is not limited thereto. For example, the analyzing portion 4 may provide the observer with data for determining the culturing states and the proliferation states by generating a time-series graph of the adhesion areas of the cells 100 or by calculating the completion rate or the like until the proliferation states of the cells 100 reach confluence, and by displaying the results on the monitor 16.

Next, a culture vessel 17 according to a modification of this embodiment will be described below with reference to the drawings.

In the description of this embodiment, portions having the same configurations as those of the above-described embodiment are given the same reference signs, and descriptions thereof will be omitted.

Figure 3:
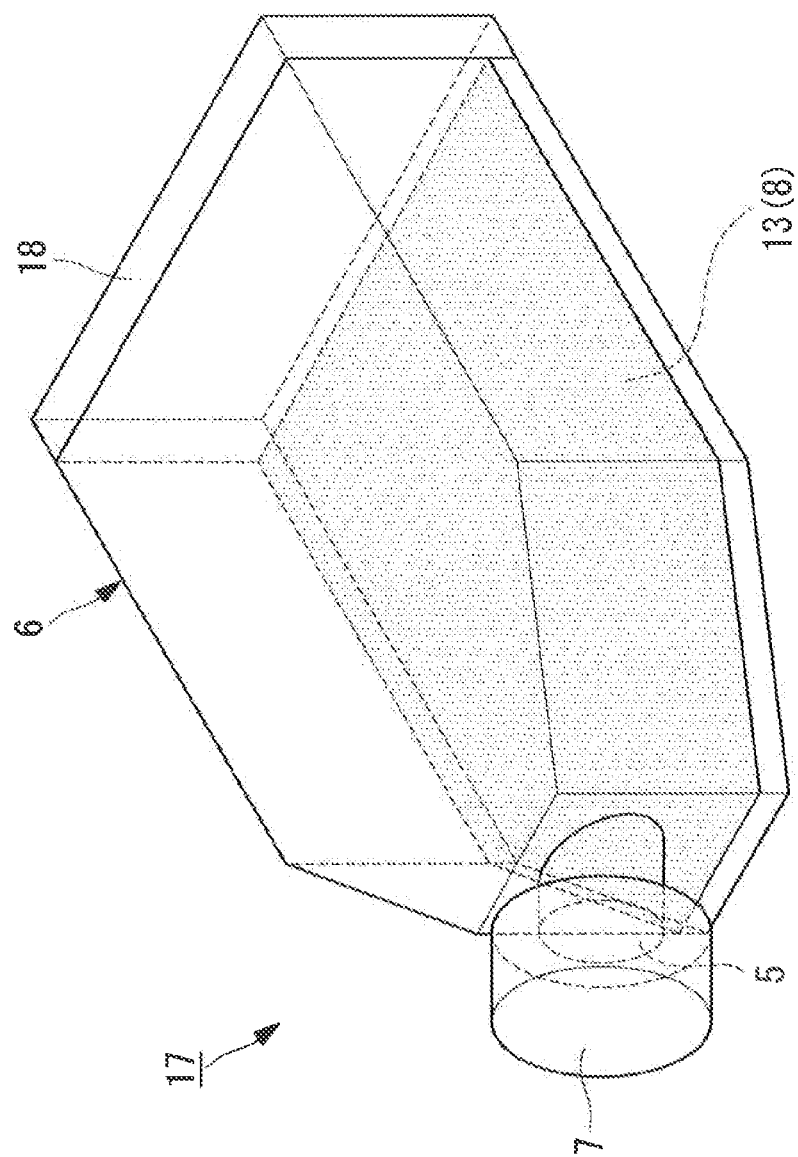
FIG. 3 is an overall configuration diagram showing a culture vessel according to a modification of the present invention.

As shown in FIG. 3, with the culture vessel (cell culture vessel) 17 according to this embodiment, the bottom 8 of the vessel main unit 6 is constituted of the touchscreen sensor 13, and a transmitting portion 18 is provided at the exterior of the vessel main unit 6.

With the thus-configured culture vessels 17 according to this embodiment, when the culture vessels 17 that accommodate the cells 100 in the interior thereof are accommodated in a general cell culturing apparatus and the cells 100 are cultured by maintaining a predetermined temperature and a predetermined humidity, as culturing advances, the cells 100 are directly adhered on the top surface of the touchscreen sensor 13 in the vessel main unit 6 and proliferate along the top surface of the touchscreen sensor 13.

At this time, the touchscreen sensor 13 detects the adhesion positions of the cells 100, and the positional information of the cells 100 is wirelessly transmitted to the exterior of the cell culturing apparatus by the transmitting portion (output portion) 18 that is provided at the exterior of the culture vessels 17. By doing so, because the positional information of the cells 100 detected by the touchscreen sensor 13 is received by the receiving portion 14 and the culturing states of the cells 100 are determined by the determining portion 15, it is possible to check the culturing states of the cells 100 in the individual culture vessels 17 on the monitor without removing the culture vessels 17 from the cell culturing apparatus.

As above, with the culture vessel 17 according to this embodiment, there is an advantage in that a general unit can be employed as the cell culturing apparatus, and thus, large-scale equipment is not necessary.

In addition, as shown in FIG. 2, with the culture vessel 17 according to this embodiment, there is an advantage in that it is possible to stack a plurality of culture vessels 17 when accommodating them in the cell culturing apparatus, instead of arranging the plurality of culture vessels 2 next to each other, and thus, it is also possible to culture numerous cells 100 at the same time.

Figure 4:
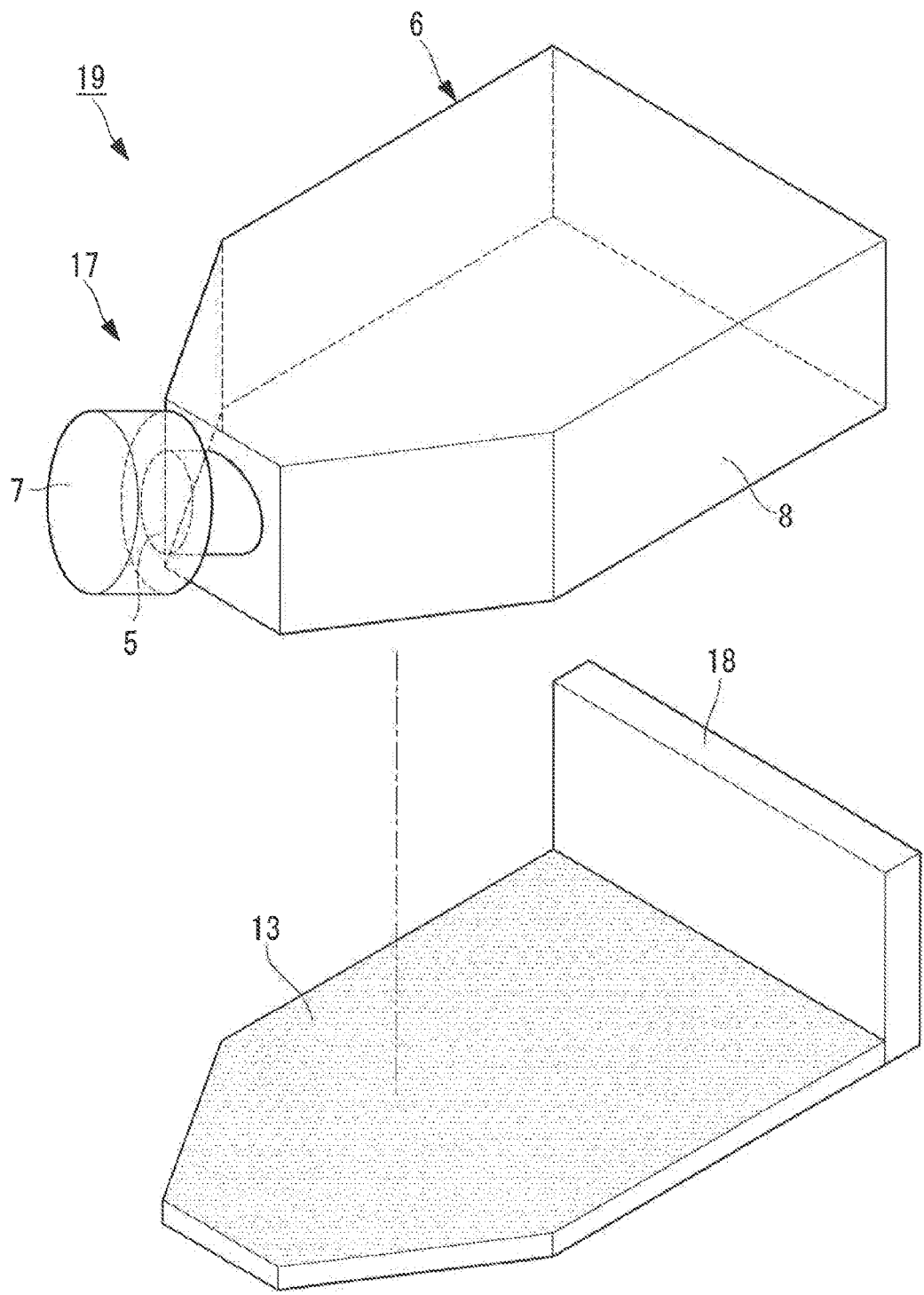
FIG. 4 is an exploded perspective view showing an example of a detector on which the culture vessel is mounted in an attachable/detachable manner.

Note that, in this embodiment, the configuration in which the touchscreen sensor 13 itself constitutes the bottom 8 of the culture vessel 17 has been described as an example; alternatively, however, as shown in FIG. 4, it is permissible to employ a detector 19 that is provided with the touchscreen sensor 13 and the transmitting portion 18 and with which the film-like bottom 8 of the culture vessel 17 is attached to the surface of the touchscreen sensor 13 in an attachable/detachable manner. By doing so, there is an advantage in that it is possible to reuse the detector 19 by employing disposable culture vessels 17.

In addition, as shown in FIGS. 2 to 4, although cases in which rectangular vessels are employed as the culture vessels 2 and 17 have been described as examples in this embodiment, the shape of vessel is not limited thereto so long as at least a surface on which the cells 100 are adhered is formed of a thin membrane-like film. For example, it is permissible to employ a dish-like vessel or the microfluidics or a bag-like (pack-like) vessel that is entirely formed of a film and to place the vessel on the touchscreen sensor 13. In this case, only the surface on which the cells 100 are adhered need be formed of a thin membrane-like film, or the entire vessel may be formed of a thin membrane-like film. In addition, the bag-like vessel may have an opening 5 and a lid 7.

With the cell culturing apparatus 1 of the present invention, in addition to detecting the culturing states, such as adhesion position and the adhesion area of the cells 100, as described above, it is also possible to detect movement of the cells 100 within a short period of time, as well as changes in electric potential (current) of the cells 100. Although an example thereof will be described below, it is not limited thereto.

For example, as a way of detecting pulsing of myocardial cells, by detecting pulses generated in the process of differentiation to myocardial cells from undifferentiated cells (for example, stem cells, induced pluripotent stem cells, or the like) by means of the touchscreen sensor 13, this serves as a way of detecting whether or not differentiation induction of the undifferentiated cells has been successful. In addition, it is also possible to detect the effects of a compound or the like on the myocardial cells.

Specifically, by adding a compound or the like to pulsing myocardial cells and by detecting the presence/absence of pulsing, it is possible to assess the effects of this compound or the like on the myocardial cells (for example, inhibition, facilitation, or the like). In this case, it is also possible to use a cell structure (for example, a cell sheet or the like formed of many types of cells) that includes the myocardial cells as an assessment subject.

In addition, by comparing against a control group, such as a group in which the cells 100 are not included, a group in which the cells 100 are not subjected to differentiation induction, or the like, it is possible to more precisely detect pulsing of the cells 100.

In addition, for example, as a way of detecting the electric potential of brain/nerve cells or myocardial cells, by detecting changes in the electric potential of the brain/nerve cells or the myocardial cells by means of the touchscreen sensor 13, it is possible to assess the activity of these cells. In addition, it is possible to detect differentiation induction to the brain/nerve cells or the myocardial cells from undifferentiated cells. At this time, by adding a compound or the like, it is possible to assess the effects of the compound or the like on the cell activity.

In addition, by comparing against a control group, such as a group in which the cells 100 are not included, a group in which the cells 100 are not subjected to differentiation induction, or the like, it is possible to more precisely detect changes in electric potential of the cells 100.

The above-described embodiment is derived from individual aspects of the present invention described below.

With this aspect, once the cells are accommodated in the culture vessel and the culture vessel is placed on the mounting surface inside the culturing chamber, the touchscreen sensor provided at the mounting surface is brought into tight contact with the external surface of the bottom of the culture vessel. By maintaining the interior of the culturing chamber at the predetermined temperature and humidity in this state, the cells in the culture vessel proliferate while being adhered to the bottom of the culture vessel. The touchscreen sensor attached to the external surface of the bottom of the culture vessel detects the adhesion positions of the cells adhered to the bottom of the culture vessel at the interior thereof. The output portion exports the detected adhesion positions of the cells to the exterior of the culturing chamber as the outputs from the touchscreen sensor. By doing so, by checking the exported adhesion positions of the cells, it is possible to easily check the adhesion area of the cells without removing the culture vessel from the culturing chamber, and thus, it is possible to check the culturing states of the cells.

In the above-described aspect, the output portion may be a transmitting portion that wirelessly transmits the output from the touchscreen sensor.

By doing so, it is possible to transmit the output from the touchscreen sensor to the exterior without making the output portion penetrate through a wall of the culturing chamber from the interior to the exterior thereof, and thus, it is possible to maintain the air-tightness of the culturing chamber.

The above-described aspect may include an input portion that is disposed at the exterior of the culturing chamber and to which the output from the touchscreen sensor exported by the output portion is input; and a determining portion that determines a culturing state of cells in the culture vessel based on the output from the touchscreen sensor which is input to the input portion.

By doing so, the output from the touchscreen sensor that is output to the exterior of the culturing chamber by the output portion is input to the input portion at the exterior of the culturing chamber, and the determining portion determines the culturing state of the cells. By doing so, it is possible to monitor the culturing state of the cells.

In the above-described aspect, the output portion may be a transmitting portion that wirelessly transmits the output from the touchscreen sensor, and the input portion may be a receiving portion that receives the output from the touchscreen sensor that is wirelessly transmitted by the transmitting portion.

By doing so, the culturing state of the cells being cultured in the culturing chamber can be monitored in a simple manner from a remote location without removing the cells from the culturing chamber.

Another aspect of the present invention is a cell culture vessel including a touchscreen sensor that is disposed at a bottom on which cells are adhered; and an output portion that outputs an output from the touchscreen sensor to an exterior thereof.

With this aspect, when the cells are accommodated and cultured in the cell culture vessel, the cells proliferate while being adhered to the touchscreen sensor at the bottom thereof. Because the touchscreen sensor detects the positions at which the cells are adhered and outputs this information to the exterior via the output portion, it is possible to monitor the culturing states of the cells for the individual cell culture vessels by monitoring the outputs that are output from the touchscreen sensor.

In the above-described aspect, the output portion is a transmitting portion that wirelessly transmits the output from the touchscreen sensor.

Another aspect of the present invention is a cell culture vessel including a bottom that is formed of a film and to which cells are attached on an internal surface thereof; and a touchscreen sensor that is brought into tight contact with an external surface of the bottom.

With this aspect, the adhesion positions of the cells that are adhered to the internal surface of the bottom formed of the film are detected, through the bottom, by the touchscreen sensor that is in tight contact with the external surface of the bottom. By doing so, it is possible to monitor the culturing states of the cells for the individual cell culture vessels while maintaining the air-tightness of the cell culture vessel.

Another aspect of the present invention is a cell culturing method including a step of accommodating cells in a culture vessel; a step of accommodating the culture vessel in a culturing chamber of a culturing apparatus in a state in which a touchscreen sensor is in tight contact with an external surface of a bottom of the culture vessel in which the cells are accommodated; and a step of observing an output from the touchscreen sensor by maintaining an interior of the culturing chamber at a predetermined temperature and humidity.

REFERENCE SIGNS LIST 1 cell culturing apparatus
2, 17 culture vessel (cell culture vessel)
8 bottom of culture vessel
9 culturing chamber
10 mounting surface
12, 18 transmitting portion (output portion)
13 touchscreen sensor
14 receiving portion (input portion)
15 determining portion

The invention claimed is:

1. A detector comprising a touchscreen sensor, wherein:
the touchscreen sensor is configured such that, when the touchscreen sensor is brought into tight contact with one side of a film of a culture vessel, the touchscreen sensor allows detection of pressure signals or electrical signals from cells adhered to the other side of the film, and
at least one surface of the culture vessel is formed of the film.

2. The detector according to claim 1, wherein the touchscreen sensor detects an adhesion position or an adhesion area of the cells through the film.

3. The detector according to claim 1, wherein the touchscreen sensor is a sensor based on a resistive membrane system or a capacitive sensing system.

4. The detector according to claim 1, wherein the culture vessel is a bag-like vessel.

5. The detector according to claim 1, wherein a material of the film is polyethylene terephthalate or silicone.

6. The detector according to claim 1, wherein a thickness of the film is 150 μm±50 μm.

7. The detector according to claim 1, wherein a resolution of the touchscreen sensor is 10 nm.

8. A culture vessel comprising a touchscreen sensor, wherein the touchscreen sensor is configured to allow detection of pressure signals or electrical signals from cells.

9. The culture vessel according to claim 8, further comprising a film, wherein the touchscreen sensor is brought into tight contact with one side of the film, and the touchscreen sensor is configured to allow detection of pressure signals or electrical signals from cells adhered to the other side of the film.

10. The culture vessel according to claim 9, wherein the touchscreen sensor detects an adhesion position or an adhesion area of the cells through the film.

11. The culture vessel according to claim 8, wherein the touchscreen sensor is a sensor based on a resistive membrane system or a capacitive sensing system.

12. The culture vessel according to claim 8, wherein the culture vessel is a bag-like vessel.

13. The culture vessel according to claim 9, wherein a material of the film is polyethylene terephthalate or silicone.

14. The culture vessel according to claim 9, wherein a thickness of the film is 150 μm±50 μm.

15. The culture vessel according to claim 8, wherein a resolution of the touchscreen sensor is 10 nm.

16. A cell detecting method for detecting cells in a culture vessel, at least one surface of the culture vessel being formed of a film, and the method comprising:
bringing a touchscreen sensor into tight contact with one side of the film, the touchscreen sensor being configured to allow detection of pressure signals or electrical signals from cells adhered to the other side of the film; and
detecting information from the cells by using the touchscreen sensor.

17. The cell detecting method according to claim 16, wherein the touchscreen sensor is a sensor based on a resistive membrane system or a capacitive sensing system.

18. The cell detecting method according to claim 16, wherein:
the cells include myocardial cells, and
in the detecting, the touchscreen sensor detects pulsing of the myocardial cells or changes in electric potential of the myocardial cells.

19. The cell detecting method according to claim 18, wherein the cells are a cell structure including the myocardial cells.

20. The cell detecting method according to claim 16, wherein:
the cells include brain/nerve cells, and
in the detecting, the touchscreen sensor detects changes in electric potential of the brain/nerve cells.

21. The cell detecting method according to claim 16, wherein a material of the film is polyethylene terephthalate or silicone.

22. The cell detecting method according to claim 16, wherein a thickness of the film is 150 μm±50 μm.

23. The cell detecting method according to claim 16, wherein a resolution of the touchscreen sensor is 10 nm.

* * * * *